United States Patent
Steinbauer et al.

(10) Patent No.: US 8,088,955 B2
(45) Date of Patent: Jan. 3, 2012

(54) ALPHA-SUBSTITUTED α,β-UNSATURATED E- OR Z-ALDEHYDES, USE THEREOF, AND PROCESSES FOR THEIR PREPARATION α,β

(75) Inventors: Gerhard Steinbauer, Enns (AT); Martina Kotthaus, Linz (AT); Klaus Edegger, Linz (AT); Stefaan Marie Andre De Wildeman, Maasmechelen (BE); Henricus Martinus Maria Gerardus Straatman, LG Horst (NL); Anna Maria Cornelia Francisca Castelijns, JB Spaubeek (NL); Andreas Hendrikus Maria De Vries, CR Maastricht (NL)

(73) Assignee: DSM Fine Chemicals Austria NFG GmbH & Co. KG, Linz (AT)

( * ) Notice: Subject to any disclaimer, the term of this patent is extended or adjusted under 35 U.S.C. 154(b) by 0 days.

(21) Appl. No.: 12/668,236

(22) PCT Filed: Jul. 11, 2008

(86) PCT No.: PCT/EP2008/059145
§ 371 (c)(1),
(2), (4) Date: Jun. 1, 2010

(87) PCT Pub. No.: WO2009/007462
PCT Pub. Date: Jan. 15, 2009

(65) Prior Publication Data
US 2010/0234630 A1    Sep. 16, 2010

(30) Foreign Application Priority Data
Jul. 11, 2007 (EP) .................................. 07013562

(51) Int. Cl.
*C07C 47/27* (2006.01)
*C07C 45/00* (2006.01)
*C07C 309/01* (2006.01)
*C07F 7/02* (2006.01)
(52) U.S. Cl. .......... 568/433; 568/442; 560/14; 564/384; 556/466
(58) Field of Classification Search .................. 568/433, 568/442; 560/14; 564/384; 556/466
See application file for complete search history.

(56) References Cited

U.S. PATENT DOCUMENTS
6,683,206 B2 * 1/2004 Stutz et al. .................. 562/465
6,881,868 B2 * 4/2005 Stutz et al. .................. 568/608

FOREIGN PATENT DOCUMENTS
WO   02/02487   1/2002
WO   02/02500   1/2002

OTHER PUBLICATIONS

International Search Report for PCT/EP2008/059145, mailed Aug. 26, 2008.
Written Opinion of the International Searching Authority for PCT/EP2008/059145, mailed Aug. 26, 2008.
Database CA [online], Chemical Abstracts Service, Columbus, Ohio, US, Takahashi et al., "Total Synthesis of Dipiperamide A and Revision of Stereochemical Assignment", XP002462675, 2005.
Database Beilstein, Beilstein Institute for Organic Chemistry, Frankfurt-Main, DE, XP002462676, 1960.

* cited by examiner

*Primary Examiner* — Sikarl Witherspoon
(74) *Attorney, Agent, or Firm* — Nixon & Vanderhye P.C.

(57) ABSTRACT

This invention relates to novel alpha-substituted α,β-unsaturated E- or Z-aldehydes, or isomer mixture thereof, of the formula (I) in which $R_1$ and $R_2$ may be identical or different and are each H or a hydrocarbon, in which the hydrocarbon may have one or more heteroatoms and $R_3$ and $R_4$ may be identical or different and are each a hydrocarbon, in which the hydrocarbon may have one or more heteroatoms, and $R_5$ may be identical or different and is H or a hydrocarbon, in which the hydrocarbon may have one or more heteroatoms, to the use thereof, and to processes for their preparation. The invention further relates to the preparation of further intermediates for pharmaceuticals and to the preparation of the pharmaceuticals.

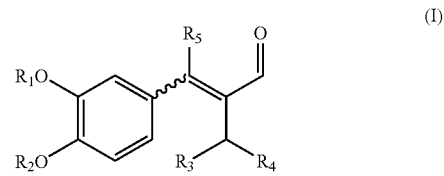

(I)

5 Claims, No Drawings

ALPHA-SUBSTITUTED α,β-UNSATURATED E- OR Z-ALDEHYDES, USE THEREOF, AND PROCESSES FOR THEIR PREPARATION α,β

This application is the U.S. national phase of International Application No. PCT/EP2008/059145, filed 11 Jul. 2008, which designated the U.S. and claims priority to European Application No. 07013562.9, filed 11 Jul. 2007, the entire contents of each of which are hereby incorporated by reference.

Alpha-substituted α,β-unsaturated E- or Z-aldehydes are valuable compounds for preparing intermediates, for instance substituted 2-alkyl-3-phenylpropanols, of pharmaceuticals, for instance for delta-amino-gamma-hydroxy-omega-arylalkanecarboxamides, which have renin-inhibiting properties, and can be used as antihypertensives in pharmaceutical formulations.

Substituted 2-alkyl-3-phenylpropanols are known, for example, from EP 1 296 912. These alcohols are prepared in several steps. First, an aldol addition or aldol condensation of the corresponding substituted benzaldehyde with an isovaleric ester is carried out. The addition or condensation product thus obtained is obtained as a diastereomer mixture in a syn/anti ratio of about 3:1. The desired syn diastereomer is, according to the literature references, obtained in crystalline form and is isolated from the reaction mixture for the further processing to give the desired end product and is removed from the anti-diastereomer. Only then is the syn-diastereomer reacted further. First, the OH group is converted to a leaving group, which is then eliminated in the presence of a strong base, which affords the corresponding α,β-unsaturated carboxylic ester. Thereafter, this ester is reduced to the corresponding α,β-unsaturated alcohol, which is then converted by hydrogenation to 2-alkyl-3-phenylpropanol.

Disadvantages of this process are firstly the necessity of isolating the syn-diastereomer after the aldol addition or condensation and the relatively low yield of the desired alpha-substituted E-cinnamic acid derivative of about 57% proceeding from the substituted benzaldehyde. The anti-diastereomer is additionally disposed of unused.

The multitude of steps required until a 2-alkyl-3-phenylpropanol is obtained and the use of expensive chemicals, for instance butyllithium, LiAlH$_4$, potassium tert-butoxide, are also disadvantageous with regard to an economically viable process.

WO 02/02500 describes the preparation of a further precursor of the 2-alkyl-3-phenylpropanols, the corresponding 2-alkyl-3-phenylpropionic acids. According to WO 02/02500, an aldol addition or aldol condensation of the corresponding substituted benzaldehyde with an isovaleric ester is likewise carried out. The addition or condensation product thus obtained is obtained as a diastereomer mixture in a syn/anti ratio of about 3:1. According to these literature references, the desired syn-diastereomer is obtained in crystalline form and is isolated from the reaction mixture and removed from the anti-diastereomer for the further processing to give the desired end product. Only then does the further conversion of the syndiastereomer proceed. First, the OH group is converted to a leaving group which is then eliminated in the presence of a strong base, which affords the corresponding α,β-unsaturated carboxylic ester. Thereafter, this ester is hydrolyzed to the corresponding α,β-unsaturated carboxylic acid. This can then be converted to a saturated carboxylic acid by hydrogenation with H$_2$ and a chiral catalyst metal complex of a metal from the group of iridium, ruthenium or rhodium, and a chiral ligand from the group of diphosphines and monophosphines. This saturated carboxylic acid can then be converted to 2-alkyl-3-phenylpropanol by reaction with LiAlH$_4$.

Disadvantages in this process are again the points already detailed above.

It is therefore an object of the present invention to find a new means of being able to prepare 2-alkyl-3-phenylpropanols in high yields in an economically viable manner.

Unexpectedly, this object is achieved by novel alpha-substituted α,β-unsaturated E- or Z-aldehyde derivatives.

The present invention accordingly provides novel alpha-substituted α,β-unsaturated E- or Z-aldehydes, or isomer mixture thereof, of the formula

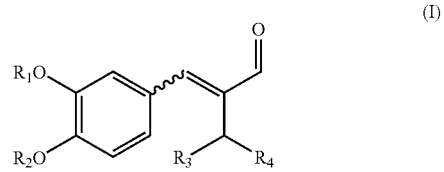

(I)

in which

R$_1$ and R$_2$ may be identical or different and are each H or an optionally substituted hydrocarbon which optionally has one or more heteroatoms, and in which R$_1$ and R$_2$ may optionally be bonded to one another to form a ring structure; and R$_3$ and R$_4$ may be identical or different and are each an optionally substituted hydrocarbon which optionally has one or more heteroatoms, and in which R$_3$ and R$_4$ may be bonded to form a ring structure.

In this application, "hydrocarbons" include substituted and unsubstituted hydrocarbons, where one hydrocarbon may have one or more heteroatoms, such as Si, S, N, O, P, Cl, Br, F, I, or may consist of carbon atoms and hydrogen atoms. The hydrocarbon may be linear or branched. The hydrocarbon may have one or more ring structures, which ring structure may be aromatic (aryl) or aliphatic (cycloalkyl). The ring structure may comprise one or more heteroatoms, especially O and/or N. The number of carbon atoms may especially be 1-20, more especially up to 12 or up to 6. If the hydrocarbon comprises a ring structure, the hydrocarbon usually has at least 3 carbon atoms.

In the formula (I), R$_1$ is preferably H or 3-methoxypropyl, or an oxygen protecting group.

R$_2$ is preferably H, an oxygen protecting group or a methyl.

Oxygen protecting groups are understood to mean customary groups for protecting the oxygen atom, for instance a tosylate, mesylate, benzoylate, benzoate, trialkylsilyl or carboxylic acid group, such as the acetate group, etc., and all other protecting groups customary for alcohols or oxygen atoms.

R$_3$ and R$_4$ may be identical or different and are each preferably C$_1$—C$_6$-alkyl, C$_1$—C$_6$-allyl or optionally substituted phenyl (maximum of 12 carbon atoms).

C$_1$—C$_6$-Alkyl is understood to mean linear or branched alkyl groups having from 1 to 6 carbon atoms, for instance methyl, ethyl, n-propyl, i-propyl, n-butyl, sec-butyl, tert-butyl, etc. Preference is given to C$_1$-C$_4$-alkyl and particular preference to methyl.

The phenyl group may optionally be substituted by C$_1$—C$_6$-alkyl, C$_1$—C$_6$-alkoxy, halogen, nitro, etc.

R$_3$ and R$_4$ are preferably identical; R$_3$ and R$_4$ are more preferably both methyl.

The inventive compounds may be present in the form of the E-isomer or else in the form of the Z-isomer or in the form of an E/Z isomer mixture.

Compounds of the formula (I) are preferably:
2-[1-[4-methoxy-3-(3-methoxypropoxy)phenyl]meth-(E)-ylidene]-3-methylbutyraldehyde or 2-[1-[4-methoxy-3-

(3-methoxypropoxy)phenyl]meth-(Z) -ylidene]-3-methylbutyraldehyde or an isomer mixture thereof, 2-[1-[3-hydroxy-4-methoxyphenyl]meth-(E)-ylidene]-3-methylbutyraldehyde or 2-[1-[3-hydroxy-4-methoxyphenyl]meth-(Z)-ylidene]-3-methylbutyraldehyde or an isomer mixture thereof, methanesulfonic acid 5-((E)-2-formyl-3-methylbut-1-enyl)-2-methoxyphenyl ester or methanesulfonic acid 5-((Z)-2-formyl-3-methylbut-1-enyl)-2-methoxyphenyl ester or an isomer mixture thereof, toluene-4-sulfonic acid 5-((E)-2-formyl-3-methylbut-1-enyl)-2-methoxyphenyl ester or toluene-4-sulfonic acid 5-((Z)-2-formyl-3-methylbut-1-enyl)-2-methoxyphenyl ester or an isomer mixture thereof, benzoic acid 5-((E)-2-formyl-3-methylbut-1-enyl)-2-methoxyphenyl ester or benzoic acid 5-((Z)-2-formyl-3-methylbut-1-enyl)-2-methoxyphenyl ester or an isomer mixture thereof, 2-[1-(3,4-dihydroxyphenyl)meth-(E)-ylidene]-3-methylbutyraldehyde or 2-[1-(3,4-dihydroxyphenyl)meth-(Z)-ylidene]-3-methylbutyraldehyde or an isomer mixture thereof, 2-[1-(4-methoxy-3-trimethylsilanyloxyphenyl)meth-(E)-ylidene]-3-methylbutyraldehyde or 2-[1-(4-methoxy-3-trimethylsilanyloxyphenyl)meth-(Z)-ylidene]-3-methylbutyraldehyde or an isomer mixture thereof.

The inventive aldehydes can be prepared in a simple, inexpensive manner. Compared to the preparation described in the prior art for the precursors to the 2-alkyl-3-phenylpropanols, the corresponding α,β-unsaturated alcohol or the corresponding α,β-unsaturated carboxylic acid, fewer reaction steps and less expensive reagents are required, and the aldehyde is obtained in higher yields.

The present invention accordingly further provides for the preparation of the inventive aldehydes of the formula (I).

The inventive aldehydes of the formula (I) in which $R_1$, $R_2$, $R_3$ and $R_4$ are each as defined in claim 1-3 are prepared by a process comprising a reaction step comprising reacting an aldehyde of the formula (IV)

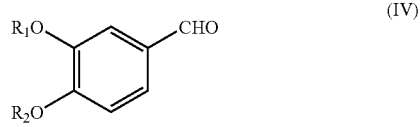

(IV)

in which $R_1$ and $R_2$ may be identical or different and are each as defined in claim 1-3, and in which $R_1$ and $R_2$ may optionally be joined to one another to form a ring structure with an aldehyde of the formula (V) or the enamine thereof,

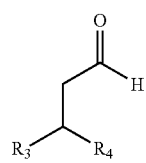

(V)

in which $R_3$ and $R_4$ are each as defined in any of claims 1 to 3.

The process for preparing the aldehydes of the invention according to formula (I) may further comprise subjecting an aldehyde of the formula (VII) (so-called aldol product)

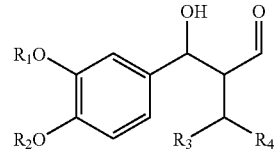

(VII)

in which $R_1$, $R_2$, $R_3$ and $R_4$ are each as defined in any of claims 1-3, and which aldehyde (VII) could be obtained by reacting an aldehyde according to formula (IV) with an aldehyde, or the enamine thereof, according to formula (V) as described above, to an elimination reaction giving the compound according to formula (I).

Such elimination reaction of aldol products are known to a person skilled in the art, and may for example be achieved by acid or base.

In order to obtain the corresponding enamine, the aldehyde of the formula (V) is dissolved in a suitable solvent, for instance toluene, DMF, DMAC, etc., and the reaction mixture is cooled to from −5° C. to 10° C. Subsequently, a solution of pyrrolidine in toluene, DMF or DMAC, etc., is slowly added dropwise and the reaction mixture is stirred at from −5° C. to 10° C.

After the reaction has ended, the solvent and volatile components are evaporated.

Optionally, the O-protecting group can then be eliminated in a customary manner either by acidic or basic means in accordance with the prior art, which affords aldehydes of the formula (I) in which $R_1$ is H and $R_3$ and $R_4$ are each as defined above.

The aldehydes of the invention according to formula (I) are obtained as an E/Z isomer mixture (approx. 70/30) and can optionally be separated by customary methods known from the prior art (for instance by preparative HPLC, crystallization, etc.).

Preference is given to using this process to prepare an aldehyde of the formula (I) in which $R_1$ is H, $R_2$ is methyl, $R_3$ and $R_4$ are methyl.

This compound is notable especially in that it is water-soluble, which subsequently enables an enzymatic reaction (for example by means of enone reductase).

When aldehydes of the formula (I) which do not have such good water solubility are obtained, the water solubility can be increased by adding base (for example organic and inorganic bases, for instance NaOH, KOH, $Ca(OH)_2$, etc.) and conversion to the corresponding salt.

The reaction for the preparation the aldehydes according to the invention is typically effected in the presence of a base, for instance NaOH, $K_2CO_3$, etc., or, when the enamine is used, optionally even without base, and in a suitable solvent, for instance toluene, DMF, water, etc. The reaction temperature is typically between 0° C. and 100° C., preferably from 20° C. to 80° C. Typically, the reaction is carried out under atmospheric pressure.

The benzaldehyde of the formula (VI) in which $R_1$ is preferably 3-methoxypropyl can be obtained by reacting the corresponding benzaldehyde of the formula

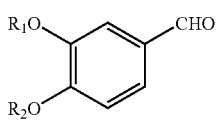

(VIII)

in which $R_1$ is preferably H and $R_2$ is preferably methyl or H with $Cl(CH_2)_3OCH_3$ in the presence of a base, for instance $K_2CO_3$, in a suitable solvent, for instance DMF, toluene, DMAC, etc., in accordance with the prior art, for example according to WO 2005/051911, EP 678500 or Tetrahedron Letters, (2005), 46(37), 6337-6340.

The benzaldehyde of the formula (VI) in which $R_1$ is a protecting group can, according to the process for protecting group introduction already described above, be obtained proceeding from the corresponding benzaldehyde of the formula (VIII).

The compound of the formula (VII) is converted to an aldehyde of the formula (I) by acidic elimination (water elimination), typically at a temperature of from 15 to 90° C., preferably at from 20 to 80° C.

The aldehyde thus prepared is in turn present as an E/Z mixture. If appropriate, the mixture can be separated into the isomers in a customary manner.

Preference is given to using this process to prepare an aldehyde of the formula (I) in which $R_1$ is methoxypropyl, $R_2$ is methyl, $R_3$ and $R_4$ are methyl.

However, the mixture of the aldehydes of the formula I, or the isomers themselves, can also be converted in a further step to the saturated aldehyde of the formula

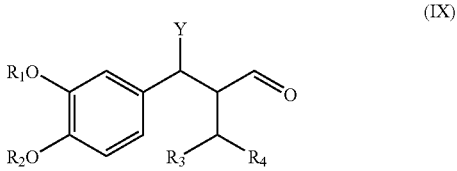

(IX)

in which $R_1$ is preferably 3-methoxypropyl or a protecting group and $R_2$ may preferably be methyl or H, and $R_3$ and $R_4$ are each as defined above.

Y is hydrogen or a conjugated base. Y is preferably selected from —H, —Cl, —Br, —I, —F, —SiR$^x$R$^y$R$^z$, —SR$^x$, —NR$^x$R$^y$, in which R$^x$, R$^y$ and R$^z$ are each independently selected from H and hydrocarbon groups, especially from H, optionally substituted $C_1$—$C_{12}$ alkyl and $C_2$$C_{12}$ alkenyl, preferably H, optionally substituted $C_1$—$C_6$ alkyl and $C_2$—$C_6$ alkenyl. Y is especially H.

The mixture of the aldehydes of the formula I, or the isomers themselves, can, however, also be converted by catalytic hydrogenation to the saturated aldehyde of the formula IX.

Suitable catalysts are known, for example from Organometallics 1991, 10, 2126-2133, or Molecular Catalysis A: Chemical 2002, 178, 181-190, or Angew. Chemie Int. Ed. 2005, 44, 108-110.

In addition, the hydrogenation can take place in the presence of a metal complex, for example a metal complex as described in EP 1 296 912. Particularly suitable metal complexes are rhodium complexes, ruthenium complexes, iridium complexes and platinum complexes.

The suitable heterogeneous catalysts include heterogeneous platinum catalysts and heterogeneous palladium catalysts, including mixtures thereof.

It is possible to add an enzyme to the hydrogenation. Enzymes suitable for this purpose are especially oxidoreductases, more especially ene reductases. For example, "old yellow" enzymes can be used (OYE, OYE2, OYE3), or the enzymes HYE1, HYE2, P1 or LTB4DH.

Suitable enzymatic systems are also described in Fardelone et al., J. Mol. Catal. B: Enzymatic 29 (2004) 41-45, Ferraboschi et al., Tetrahedron:Asymmetry 10(1999) 2639; Mano et al., in Plant & Cell Physiology, 43(12):1445-1455 (2002) or Hall et al., Angewandte Chemie 2007, 46, 3934-3937.

The present invention further provides for the use of the aldehydes of the formula (I) to prepare 2-(R)- or (S)-alkyl-3-phenylpropionaldehydes of the formula (IX), or an enantiomer mixture in which $R_1$, $R_2$, $R_3$, $R_4$ are as defined in claim 1 and Y is H or a conjugated base.

The aldehydes of the formula IX are prepared especially with the 2(R) configuration.

An aldehyde of the formula (IX) can then be converted to the corresponding propanol of the formula (II) by catalytic hydrogenation or by reaction with $NaBH_4$.

An inventive aldehyde of the formula I is outstandingly suitable for preparing the corresponding saturated aldehyde, for preparing the corresponding saturated alcohols, or for preparing the corresponding unsaturated alcohols. For example, 2-alkyl-3-phenylpropanols can in turn be converted to the corresponding 1-halo-2-alkyl-3-phenylpropanes, especially to the corresponding 1-chloro-2-alkyl-3-phenylpropanes.

Further derivatives and corresponding halodehydroxylated compounds can be prepared, for example, from the alcohols. Such halodehydroxylated compounds are outstanding intermediates for preparing pharmaceuticals, for example for preparing pharmaceutically active compounds for delta-amino-gamma-hydroxy-omega -arylalkanecarboxyamides, especially aliskiren.

The present invention further provides for the use of the aldehydes of the formula (I) to prepare 2-(R)- or (S)-alkyl-3-phenylpropanols or an enantiomer mixture of the formula (II),

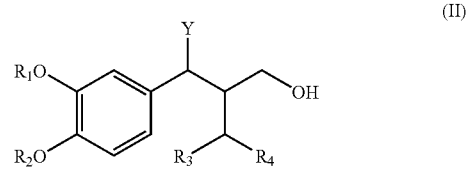

(II)

in which $R_1$, $R_2$, $R_3$ and $R_4$ are each as defined in claim 1 and Y is H or a conjugated base.

The aldehydes of the formula (I) are particularly suitable for preparing propanols of the formula (II) in which $R_1$ is 3-methoxypropyl and $R_2$ is methyl.

Particular preference is given to preparing propanols of the formula (II) in which $R_1$ is 3-methoxypropyl, $R_2$ is methyl, $R_3$ and $R_4$ are both methyl and Y is H.

The propanols of the formula (II) with Y=H are present in the form of the (R) or (S) compounds or in the form of an enantiomeric mixture.

In particular, the propanols of the formula (II) are prepared with an enantiomeric excess of the (R) configuration.

The propanols of the formula (II) can be prepared, for example, as follows:
when, for example, the starting material is an aldehyde of the formula (I) in which $R_1$ is H and $R_2$ is methyl, the corresponding alcohol where $R_1$ is H and $R_2$ is methyl is first prepared, for instance enzymatically by enone reductase and alcohol dehydrogenase, or by catalytic asymmetric hydrogenation, and is then converted to the desired alcohol of the formula (II) in which $R_1$ is 3-methoxypropyl by reaction with $Cl(CH_2)_3OCH_3$ in the presence of a base, for instance $K_2CO_3$, in a suitable solvent, for instance DMF, toluene, with a phase transfer catalyst, N,N-dimethylacetamide (DMAC), etc., in accordance with the prior art, for example according to WO 2005/051911, EP 678500 or Tetrahedron Letters, (2005), 46(37), 6337-6340.

The invention also relates to a process for preparing a compound of the formula (II) from an aldehyde of the formula (I) where E and Z isomers are converted to the compound of the formula (II), especially in the presence of chiral hydrogenation catalysts from the group of enzymes or homogeneous catalysts, or a mixture thereof. When the starting material is an aldehyde of the formula (I), in which $R_1$ preferably is 3-methoxypropyl and $R_2$ preferably is methyl, the desired enantiomerically enriched propanol is prepared by catalytic hydrogenation to give the saturated aldehyde and subsequent catalytic hydrogenation of the aldehyde group in the presence of a catalyst, for example an enzyme, especially an alcohol dehydrogenase, or a homogeneous catalyst prepared from a metal and a chiral ligand, in which a ligand is a compound that adds electrons onto the metal, for example a phosphine, bisphosphine, diphosphine, monophosphine, bisamine or diamine, especially a chiral ruthenium catalyst.

The invention further provides for the catalytic reduction of the aldehyde of the formula (I), the E aldehyde, the Z aldehyde or the mixture, to the aldehyde of the formula (IX), or equally to the propanol of the formula (II), in the presence of a compound with isomerizing properties. Such a compound is capable of participating in a Michael addition and in a retro-Michael addition, more preferably this compound is selected from the group of thiols, including thioalkohols; halogens; secondary amines; and tertiary amines.

In particular, the compounds of the formula (IX) and of the formula (II) are prepared in an enantiomeric excess, more especially with the (R) configuration.

The propanols of the formula (II) can also be prepared from racemic or enantiomerically enriched aldehyde of the formula (IX) by catalytic reduction of the aldehyde group under reaction conditions which cause racemization, especially with an enzyme or homogeneous ruthenium catalyst.

Reaction conditions which cause racemization are, for example, produced by the addition of an acid or a base, for example by addition of a secondary amine, more particularly a cyclic secondary amine, for example pyrrolidines.

A compound of the formula I is suitable for preparing a compound of the formula (XVIII),

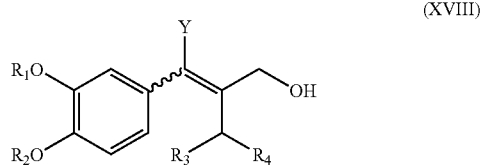
(XVIII)

in which $R_1$, $R_2$, $R_3$ and $R_4$ are as defined in claim 1 and Y is H or a conjugated base, by reduction of the aldehyde group of a compound of the formula (I). The carbonyl-selective reduction of the compound of the formula (I) to the compound of the formula (XVIII) can be carried out by various methods known to those skilled in the art. Examples of such methods include hydride-transferring reagents or catalysts, for example main group element hydrides or transition metal complexes which can act as a catalyst, transfer hydrogenations, reductions with metals or low-valency metal salts, diimine reductions or hydrogenations. A review of such processes is given, for example, in R. L. Larock, Comprehensive Organic Transformations, Wiley-VCH, New York, 1999.

As described above, a compound of the formula (II)

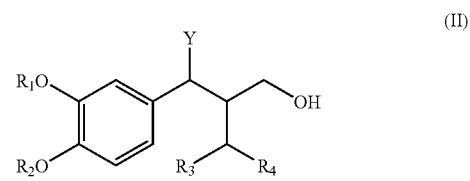
(II)

can be prepared from an aldehyde of the formula (I). It is also possible to prepare this compound from a compound of the formula (IX) by reduction of the aldehyde group or from a compound of the formula (XVIII) by reduction of the carbon-carbon double bond indicated. The reduction can be carried out by various methods known to those skilled in the art.

This compound of the formula (II) can also be used to prepare a compound of the formula (X)

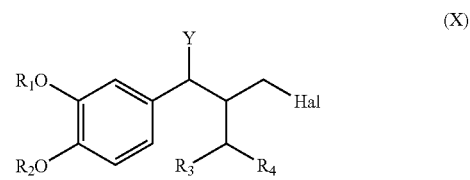
(X)

in which $R_1$, $R_2$, $R_3$ and $R_4$ are as defined in claim 1, Y is H or a conjugated base and Hal is a halogen atom, preferably chlorine. For this purpose, halodehydroxylation is suitable. A suitable process for this purpose is described in Tetrahedon Letters 2000, 41, 10085-10089 and 10091-10094.

It is also possible to prepare a compound of the formula (X) by converting the alcohol of a compound of the formula (II) to a leaving group and replacing the leaving group with a halogen. Suitable leaving groups are especially alkylsulfonate, for example methanesulfonate.

Next, a compound of the formula (XI)

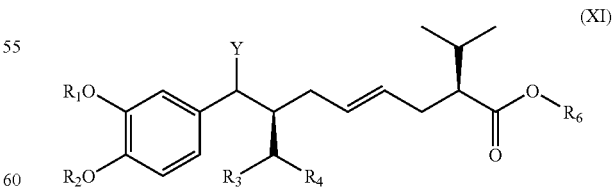
(XI)

in which $R_1$, $R_2$, $R_3$ and $R_4$ are as defined in claim 1, Y is H or a conjugated base, $R_6$ is H, $C_1$-$C_{12}$ alkyl, preferably $C_1$-$C_6$ alkyl, and with more preference $R_6$ is H, methyl or t-butyl, can be prepared from a 1-halo-2-alkyl-3-phenylpropane of the formula (X) by reaction with a compound of the formula (XII)

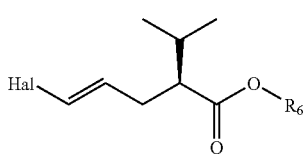
(XII)

in which Hal is a halogen, preferably chlorine and $R_6$ is as defined for formula (XI).

Such a reaction takes place in the presence of a Grignard reagent. This reaction preferably takes place in the presence of a first metal, such as magnesium, zinc or lithium, and of a transition metal different from the first metal. The transition metal is preferably a metal of group VIII, especially selected from the group of manganese, copper, iron, nickel and palladium. Particular preference is given to a metal selected from the group of iron, nickel, palladium and copper.

Such a reaction can be carried out as described in WO 02/02508.

If appropriate, it is possible to prepare a further compound from a compound of the formula XII, for example in a manner analogous to a process as described in WO 02/02508.

In particular, next, a compound of the formula (XIII),

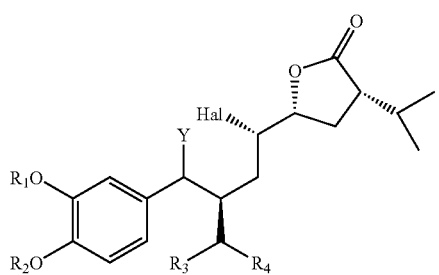
(XIII)

in which $R_1$, $R_2$, $R_3$ and $R_4$ are as defined in claim 1, Y is H or a conjugated base and Hal is a halogen atom, can be prepared from a compound of the formula (XI).

If Y is hydrogen, the compound of the formula (XI) can be halogenated directly and lactonized. The halogenation takes place in the presence of a halogenating agent, preferably a brominating agent, such as N-bromosuccinimide, in a solvent, for example dichloromethane. Preferably, the halogen atom Hal in formula (XIII) is bromine.

Next, a compound of the formula (XIII) can be used to prepare a compound of the formula (XIV),

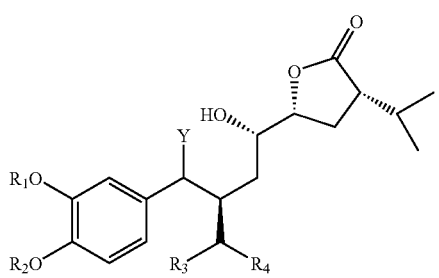
(XIV)

in which $R_1$, $R_2$, $R_3$ and $R_4$ are as defined in claim 1 and Y is H or a conjugated base, by replacing the halogen (for example bromine) with hydroxide. This takes place in the presence of a hydroxide-containing solution, such as an NaOH or KOH solution (for example 1 M in water).

By replacing the hydroxide with an azide in this compound of the formula (XIV), a compound of the formula (XV)

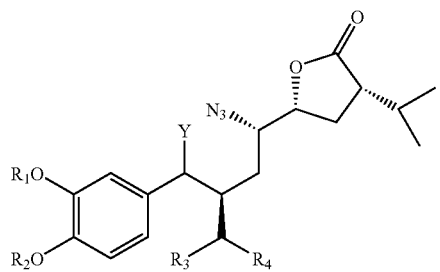
(XV)

in which $R_1$, $R_2$, $R_3$ and $R_4$ are as defined in claim 1 and Y is H or a conjugated base is prepared.

A direct reaction with activated azide is possible. In particular, metal azides are suitable. In a preferred process, sodium azide is used.

It is also possible first to convert a compound of the formula (XIV) to a compound of the formula (XIX)

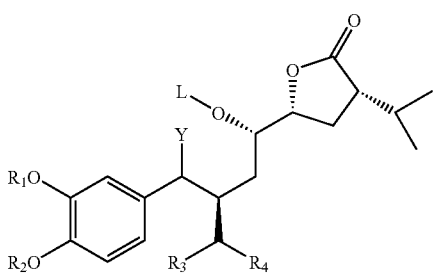
(XIX)

in which $R_1$, $R_2$, $R_3$ and $R_4$ are as defined in claim 1, Y is H or a conjugated base and L is a leaving group, especially an alkylsulfonate group, such as $CH_3$—$SO_3$—. The reaction can be conducted with a salt of the L group (such as mesylate chloride), for example in triethylamine in the presence of an amine.

This compound of the formula (XIX) can be reacted with the azide, for example to form a compound of the formula (XV).

The azide compound of the formula (XV) can next be used to prepare a compound of the formula (XVI)

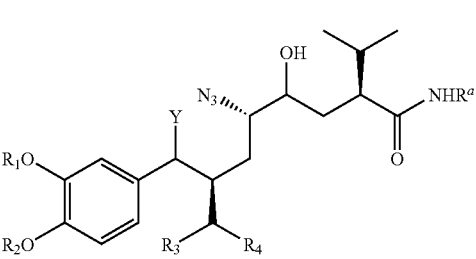
(XVI)

in which $R_1$, $R_2$, $R_3$ and $R_4$ are as defined in claim 1 and Y is H or a conjugated base by reaction with $H_2NR^a$, for example in triethylamine, in the presence of 2-hydroxypyridine. $R^a$ is H or an optionally substituted hydrocarbon which optionally has one or more heteroatoms. $R^a$ is preferably —$(CH_2)_x$CO—$NH_2$ where x is 3-6; more preferably, $R^a$ is —$CH_2$—[CH$(CH_3)_2$]—CO—$NH_2$.

Next, the azide group can be reduced with hydrogen, which forms a compound of the formula (XVII) in which $R_1$, $R_2$, $R_3$ and $R_4$ are as defined in claim 1, Y is H or a conjugated base and $R^a$ is as defined above. This reduction typically takes place in the presence of a hydrogenation catalyst, such as a palladium catalyst, for example on a carbon support. This reaction preferably takes place in the presence of ethanolamine.

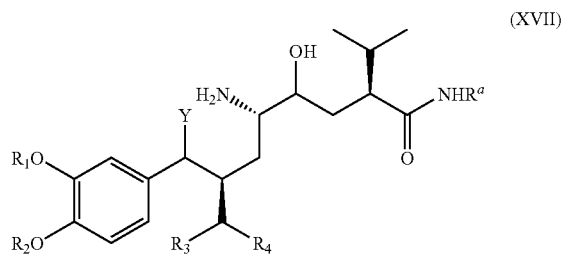

(XVII)

This hydrogenation can be conducted in the presence of an acid, such as fumaric acid, or the product can be mixed with an acid thereafter.

This forms a corresponding salt.

EXAMPLE 1

Preparation of a Compound of the Formula (I) (E/Z Mixture) ($R_1$=3-Methoxypropyl)

a) Preparation of pyrrolidino-3-methylbut-1-ene (enamine)
194 g (2.25 mol) of isovaleraldehyde are diluted in 1115 ml of toluene and cooled to 0° C. with stirring. 190.3 g (2.68 mol) of pyrrolidine, dissolved in 185.8 ml of toluene, were then added dropwise to this solution, such that the reaction temperature did not rise above 5° C. After the addition had ended, the reaction solution was stirred at 5° C. for another 1 hour. Subsequently, the mixture was warmed to room temperature and the water formed was removed completely by extraction with toluene. Thereafter, the solvent was removed by evaporation and the crude product (329.1 g; 95% of theory) was stored at 4° C. in a refrigerator.

b) Reaction of enamine with 4-methoxy-3-(3-methoxypropoxy)benzaldehyde (A1)
222.3 g (0.99 mol) of A1 were diluted with 240 g of 2-propanol. 321.2 g (2.31 mol) of the enamine, prepared in example 1a, were added to this solution at room temperature with stirring. The reaction mixture was then heated to 80° C. and stirred at this temperature for 50 hours. In order to remove unreacted A1, the reaction mixture was extracted with 1170 ml of $NaHSO_3$ (40%) and 1365 ml of water for 30 minutes.

The excess of enamine was removed by distillation using a Rotavapor and entrained out with 2-propanol (40 mbar, 50° C.). After an aqueous extraction, 148.4 g of aldehyde according to formula (I) (51.2%) were isolated.

EXAMPLE 2

Preparation of a Compound of the Formula (I) (E/Z Mixture) ($R_1$=Methanesulphonyl)

60 g (394 mmol) of isovanillin were dissolved in 200 ml of DMF and cooled to 0° C. 120 g of $Et_3N$ were added and 63 g (550 mmol) of methanesulphonyl chloride were slowly added dropwise. Subsequently, the mixture was extracted with EtOAc and HCl, and then concentrated to dryness by rotary evaporation (60° C., 10 mbar). Yield 83 g (92% of theory).

83 g (360 mmol) of mesylated isovanillin were dissolved in 250 ml of DMF and 250 ml of toluene and reacted with 90 g (646 mmol) of enamine, prepared according to Example 1a, at 60° C. with stirring.

Subsequently, the solvent was drawn off by means of a Rotavapor. Yield 70 g (65% of theory).

EXAMPLE 3

Preparation of a Compound of the Formula (II)

2-(3-(3-Methoxypropoxy)-4-methoxybenzylidene)-3-methylbutanal (E/Z mixture, ratio 3.2:1, 0.1 mmol), sodium tert-butoxide, and (R)-4-isopropyl-2-[(R)-2-(diphenylphosphino)ferrocen-1-yl]oxazoline triphenylphosphino Ru(II) dichloride (known as Naud's catalyst, 0.01 mmol) were dissolved in 5 ml of isopropanol in a glass tube.

The tube was inserted into an autoclave and a nitrogen atmosphere was applied. Five inertization cycles were followed by the application of 20 bar of hydrogen at 25° C. for 13 hours. The pressure was released and the sample exhibited complete conversion, and 95% fully hydrogenated product (2-(3-(3-methoxypropoxy)-4-methoxybenzyl)-3-methylbutan-1-ol), with an e.e. of 17%.

EXAMPLE 4

Method for the Preparation of 2-(3-(Methoxypropoxy)

-4-Methoxybenzyl)-3-Methylbutanol by 4-Electron Bioreduction of 2-(3-(Methoxypropoxy)-4-Methoxybenzylidene)-3-Methylbutanal with E.Coli Cells Expressing Enone Reductase (ER), E.Coli TOP10 Cells Expressing Alcohol Dehydrogenase (ADH), Adding Glucose Dehydrogenase (GDH from Bacillus Megaterium Purchased at Jülich Chiral Solutions) for Cofactor Recycle, Yielding Highly Enantiomerically Enriched Saturated Alcohol (According to Formula (II))

The example focuses on the production of enantio-enriched saturated alcohol under isomerising conditions starting from the E/Z mixture of 2-(3-(methoxypropoxy)-4-methoxybenzylidene)-3-methylbutanal. 1,4 dithio-DL-threitol (DTT) is used as isomerisation catalyst.

Conditions:
Atmospheric pressure, 25° C., pH=7.5 (pH adjustment with NaOH)

Ingredients Needed:
2-(3-(methoxypropoxy)-4-methoxybenzylidene)-3-methylbutanal (151.1 mg oil, purity=95%, E/Z ratio=74/26), Potassium phosphate buffer 100 mM pH=7.5 (27 ml), $NADP^+$(25 mg), Cell free extract (prepared via sonification) of E.coli TOP10 cells (purchased at Invitrogen) expressing Enone Reductase P1 (3 ml cell free extract, equivalent with 230 mg cell wet weight, 25% over-expression of total protein), cell free extract (prepared via sonification) of E.coli TOP10 cells expressing ADH E7 (1 ml cell free extract, equivalent with 80 mg cell wet weight, 30% over-expression of total protein), glucose dehydrogenase (400 units), glucose (200 mg), 1,4 dithio -DL-threitol (DTT, 1 ml of 1M solution in water). All over-expression experiments were carried out following Invitrogen protocols at www.invitrogen.com for Gateway cloning.

Results:

After 24 hr 2-(3-(methoxypropoxy)-4-methoxybenzylidene)-3-methylbutanal conversion was >99%, almost closing the carbon balance with the saturated alcohol (4-electron reduced product). As a result, >90% of the almost completely converted substrate had been converted to the (R)-enantiomer of the corresponding saturated alcohol (e.e.=82%).

EXAMPLE 5

Preparation of 2-(3-(Methoxypropoxy)-4-Methoxybenzyl)-3-Methylbutanal (A Compound According to Formula (IX))

A solution of 2-(3-(methoxypropoxy)-4-methoxybenzylidene)-3-methylbutanal (7.0 mmol, 74% E and 26% Z), tetrarhodium dodecacabonyl (0.14 mmol), (2R,3R)-(+)-2,3-Bis-(Diphenylphosphino)butane (R, R-Chiraphos, 0.63 mmol) and 300 ul triethylamine in toluene (75 ml) was transferred into an autoclave. The mixture was hydrogenated at 70-80° C. and 20 bar $H_2$. After 42 hr additional tetrarhodium dodecacarbonyl (0.14 mmol) was added to complete the reaction in 62 hr. The mixture was concentrated to 3.5 g black oil and purified by flash chromatography (heptane/ethyl acetate=2/1). Yield=1.6 g yellow oil (74%).

$^1$H NMR (CDCl$_3$) δ 1.02 (d, J=3.4, 3H), 1.04 (d, J=3.4, 3H), 2.03-2.14 (m, 3H), 2.43-2.51 (m, 1H), 2.67-2.74 (dd, 1H), 2.89-2.96 (dd, 1H), 3.36 (s, 3H), 3.58 (t, J=6.1, 2H), 3.83 (s, 3H), 4.09 (t, J=6.5, 2H), 6.68-6.79 (ar, 3H), 9.68 (d, J=2.6, 1H).

$^{13}$C NMR δ 20.1, 20.3, 28.7, 30.0, 32.1, 56.5, 59.0, 60.1, 66.5, 69.7, 112.4, 114.7, 121.5, 132.6, 148.4, 149.9, 205.5

EXAMPLE 6

Preparation of 2-(3-(Methoxypropoxy)-4-(2-(Chloromethyl)-3-Methylbutyl)-1-Methoxybenzene (A Compound According to Formula (X)) from 2-(3-(Methoxypropoxy)-4-Methoxybenzyl)-3-Methylbutanol (A Compound According to the Formula (II))

2-(3-(methoxypropoxy)-4-methoxybenzyl)-3-methylbutanol (45 g) was dissolved in toluene (52 mL) and triethylamine (16.9 g) was added as base. Next mesylchloride (13 mL) was added dropwise at room temperature and the reaction mixture was stirred for 30 minutes to complete the mesylating reaction. After the conversion was completed, DMF (47 mL), and sodiumchloride (17.6 g) were added to the reaction mixture and the mixture was heated to 100-120° C. for 2 hr. Na-mesylate was obtained as by-product.

The reaction mixture was cooled to 50° C., and at this temperature the reaction mixture was twice extracted with $H_2O$ (150 and 100 mL, respectively). The toluene layer was treated with 0.9 g of active coal, filtered, and evaporated. The residue was dissolved in 2-Propanol (115 mL) at 50° C., filtered, and cooled to −10° C. (cooling process in total is 8 hr). The crystals were isolated by filtration, washed with cold 2-Propanol (−10° C.)(2 times 45 mL) and dried at 35° C. under vacuum conditions (5 mbar). Yield: 39 g (82%) of 2-(3-(methoxypropoxy)-4-(2-(chloromethyl)-3-methylbutyl)-1-methoxybenzene.

The invention claimed is:

1. An alpha-substituted α,β-unsaturated E- or Z-aldehyde or isomeric mixture thereof of the formula (I), or the corresponding salt,

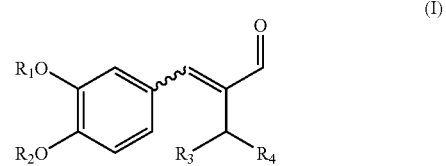

in which

R$_1$ and R$_2$ may be identical or different and are each H or an optionally substituted hydrocarbon which optionally has one or more heteroatoms, in which the hydrocarbon may especially be an oxygen protecting group, and in which R$_1$ and R$_2$ may optionally be bonded to one another to form a ring structure; and R$_3$ and R$_4$ may be identical or different and are each an optionally substituted hydrocarbon with 1-6 C atoms, which optionally has one or more heteroatoms, and in which R$_3$ and R$_4$ may be bonded to form a ring structure.

2. An alpha-substituted aldehyde according to claim 1 or the corresponding salt, in which R$_1$ is H, 3-methoxypropyl or an oxygen protecting group and in which R$_2$ is H, methyl or an oxygen protecting group and in which R$_3$ and R$_4$ are each methyl.

3. An alpha-substituted aldehyde according to claim 1, selected from the group of: 2-[1-[4-methoxy-3-(3-methoxypropoxy)phenyl]meth-(E)-ylidene]-3-methylbutyraldehyde or 2-[1 -[4-methoxy-3-(3-methoxypropoxy)phenyl]meth-(Z) -ylidene]-3-methylbutyraldehyde or an isomer mixture thereof, 2-[1 -[3-hydroxy-4-methoxyphenyl]meth-(E)-ylidene]-3-methylbutyraldehyde or 2-[1-[3-hydroxy-4-methoxyphenyl]meth-(Z)-ylidene]-3-methylbutyraldehyde or an isomer mixture thereof, methanesulfonic acid 5-((E)-2-formyl-3-methylbut-1-enyl)-2-methoxyphenyl ester or methanesulfonic acid 5-((Z)-2-formyl-3-methylbut-1-enyl)-2-methoxyphenyl ester or an isomer mixture thereof, toluene-4-sulfonic acid 5-((E)-2-formyl-3-methylbut-1-enyl)-2-methoxyphenyl ester or toluene-4-sulfonic acid 5-((Z)-2-formyl-3-methylbut -1-enyl)-2-methoxyphenyl ester or an isomer mixture thereof, benzoic acid 5((E)-2-formyl-3-methylbut-1-enyl)-2-methoxyphenyl ester or benzoic acid 5-((Z)-2-formyl-3-methylbut-1-enyl)-2-methoxyphenyl ester or an isomer mixture thereof, 2-[1-(3,4-dihydroxyphenyl)meth-(E)-ylidene]-3-methylbutyraldehyde or 2-[1-(3,4-dihydroxyphenyl)meth-(Z)-ylidene]-3-methylbutyraldehyde or an isomer mixture thereof, 2-[1-(4-methoxy-3-trimethylsilanyloxyphenyl)meth-(E)-ylidene]-3-methylbutyraldehyde or 2-[1-(4-methoxy-3-trimethylsilanyloxyphenyl)meth -(Z)-ylidene]-3-methylbutyraldehyde or an isomer mixture thereof.

4. A process for preparing an aldehyde of the formula (I) which comprises reacting an aldehyde of the formula (IV)

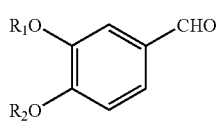

(IV)

in which $R_1$ and $R_2$ may be identical or different and are each H or an optionally substituted hydrocarbon which optionally has one or more heteroatoms, and in which $R_1$ and $R_2$ may optionally be joined to one another to form a ring structure
with an aldehyde of the formula (V) or the enamine thereof,

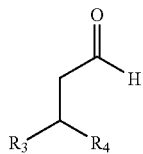

(V)

in which $R_3$ and $R_4$ are each as defined in claim 1.

5. A process according to claim 4, in which formula (IV) is a benzaldehyde with $R_1$ being 3-methoxypropyl or an oxygen protecting group and $R_2$ may be a hydrocarbon, preferably methyl or H, which gives an aldehyde of the formula (VII)

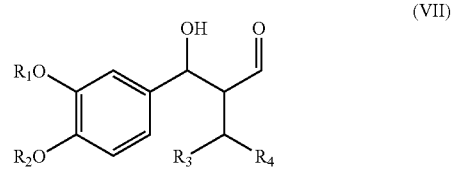

(VII)

in which $R_3$ and $R_4$ may be identical or different and are each an optionally substituted hydrocarbon with 1-6 C atoms, which optionally has one or more heteroatoms, and in which $R_3$ and $R_4$ may be bonded to form a ring structure and then converting the compound of the formula (VII) to an aldehyde of the formula (I) by acidic elimination.

* * * * *